United States Patent [19]

Teodorescu et al.

[11] 4,402,934

[45] Sep. 6, 1983

[54] DIAGNOSTIC TECHNIQUE FOR RHEUMATOID ARTHRITIS

[76] Inventors: Marius C. Teodorescu, 10547 Essex, Westchester, Ill. 60153; John L. Skosey, 4932 S. Kimbark, Chicago, Ill. 60615; Jin-Lai Chang, 1648 Gilberto Dr., Glendale Heights, Ill. 60137

[21] Appl. No.: 202,117

[22] Filed: Oct. 30, 1980

[51] Int. Cl.$^3$ .................... G01N 33/48; G01N 33/58; C12N 5/02
[52] U.S. Cl. .................................. 424/1; 435/7; 436/509; 436/804; 436/808; 424/1.5; 435/240; 435/241; 435/244; 435/810; 435/2
[58] Field of Search .................. 424/1, 101; 435/240, 435/241; 23/230 B

[56] References Cited

U.S. PATENT DOCUMENTS 4,302,437 11/1981 Herbert .................................. 424/1
4,314,987 2/1982 Morris et al. ......................... 424/1

OTHER PUBLICATIONS

International Archives of Allergy and Applied Immunology, vol. 66, pp. 1–12, (1981), Teodorescu et al.
Clinical Research, vol. 27, p. 694 (1979), Teodorescu et al.
Cellular Immunology, vol. 44, pp. 209–218 (1979), Buchholz et al.
Journal of Immunology, vol. 119 (4), pp. 1534–1537 (1977), Cohen et al.
Cohen, P. L. and 21FF, M., *J. of Immunol.*, vol. 119, No. 4, 10–77, "Abnormal Polyclonal B Cell Activation in N2V/N2WF, Mice".
Teodorescu, M. et al., *Clin. Res.*, vol. 27, pp. 694aff, 1979, "Polyclonal B Cell Activator in the Serum of Patients with Rheumatic Diseases".
Buchholz, D. M. et al., *Immunology*, vol. 37, p. 731, 08–79 "Dependence of Lymphocyte Surface on Continuous Polyclonal Activation".
Buchholz, D. M. et al., *Cellular Immunology*, vol. 44, p. 209–1979, "T–Independent but not T–Dependent Antigens Maintain Surface Ig . . . ".

*Primary Examiner*—Benjamin R. Padgett
*Assistant Examiner*—M. Morbowitz
*Attorney, Agent, or Firm*—Philip Hill

[57] ABSTRACT

A method for diagnosis of rheumatoid arthritis and related diseases comprises determination of polyclonal lymphocyte activation in B-cells cultured in the presence of patient serum. A diagnostic kit is also provided.

10 Claims, No Drawings

DIAGNOSTIC TECHNIQUE FOR RHEUMATOID ARTHRITIS

The invention described herein was made in the course of work funded in part by a grant from the National Institutes of Health.

BACKGROUND OF THE INVENTION

Rheumatic diseases affect a significant proportion of the population, crippling many people and having only a palliative treatment at best. Diagnosis of rheumatic diseases is difficult and uncertain, and many patients escape classification until the disease has progressed to a stage where serious damage is evident. The classification of the different rheumatic diseases, including rheumatoid arthritis, is based on both clinical and laboratory data, and the same criteria are used to determine the efficiency of any selected treatment. In all of the rheumatic diseases, the common denominator is an abnormal function of the immune system. This abnormal function is suggested by the appearance of antibodies against a patient's own structures and also by the beneficial effect of immunosuppressive or cytotoxic drugs which destroy cells involved in the immune mechanisms.

It has been shown that in some of these diseases the B-cells that produce antibodies are overactive, and produce antibodies against a variety of antigens, including some to which they may not have been previously exposed. Another relatively common feature is the increase in the serum immunoglobulin with polyclonal character. From such observations, it has been ascertained that B-cells programmed to produce antibodies against self antigens are present in normal individuals. It has likewise been suggested that polyclonal B-cell activation may be the cause of some autoimmune diseases.

Despite such studies of rheumatic diseases, there remains a critical need for a diagnostic technique capable of providing, with suitable certainty, an early diagnosis of the incidence of such diseases. This is especially true of the crippling diseases, such as, particularly, rheumatoid arthritis.

SUMMARY OF THE INVENTION

This invention provides a novel method for diagnosing rheumatoid arthritis and related diseases in a human patient, comprising the steps of:

(a) providing a lymphocyte population, comprising B-cells, suspended in a culture medium;

(b) adding to the B-cell suspension with mixing a portion of serum taken from said patient;

(c) cultivating in vitro the resulting mixture of serum and B-cell suspension; and (d) determining the extent of polyclonal lymphocyte activation exhibited by the B-cells in said mixture.

It is an object of this invention to provide a reliable method for early diagnosis and detection of rheumatoid arthritis.

It is a further object of this invention to provide a convenient and relatively inexpensive method for the ascertainment of the presence or absence of rheumatoid arthritis.

It is a still further object of this invention to provide diagnostic means, in the form of an assay kit, for the ready determination of the presence of rheumatoid arthritis in a patient, and suitable for use in the hands of a suitably trained clinical laboratory assistant.

DESCRIPTION OF THE INVENTION

The presence of a polyclonal B-cell activator in the serum of patients having rheumatoid arthritis has been confirmed by three distinct methods, relying respectively upon (a) the ability of the activator to maintain the surface immunoglobulin of rabbit or human B-cells in vitro; (b) the induction of blast transformation in human B lymphocyte cultures; and (c) the stimulation of nude mouse spleen cells in vitro. Similarly, negative results were obtained by all three methods when employing the serum of normal individuals or of patients having arthritis in which autoimmune phenomena had not been demonstrated.

The entire polyclonal B-cell activation agent in rheumatoid arthritis patient serum has been found to be associated with the macroglobulin fraction obtained by chromatography. It was precipitated by rabbit anti-human $\alpha_2$-macroglobulin but not by rabbit anti-immunoglobulin antibody. When $\alpha_2$-macroglobulin from patient serum was purified, the entire activity was found in this fraction. In contrast, normal $\alpha_2$-macroglobulin prepared by the same procedure exhibited no polyclonal B-cell activation activity. Thus it has been conclusively shown that there exists a polyclonal B-cell activator associated with $\alpha_2$-macroglobulin in the serum of patients having rheumatoid arthritis.

This unexpected demonstration of an activity peculiar to the serum of rheumatoid arthritis patients provides the basis for a novel and eminently useful diagnostic technique whereby it becomes possible to detect the presence of this crippling form of arthritis at an early stage in its development.

The technique, or method, of this invention successfully identifies the presence of polyclonal B-cell activation at remarkably low concentrations, thus greatly improving the sensitivity of available diagnostic methods. It has further been demonstrated that the method of this invention affords specific, reproducible, and reliable results.

Briefly, the technique of this invention requires the cultivation of a lymphocyte population, comprising B-cells, in the presence of a patient serum sample, or fraction thereof, and thereafter determining the extent of polyclonal B-cell activation. The lymphocyte population may be based upon any of a variety of B-cell sources, including, for example, rabbit, human, and nude mouse spleen B-cells. Cultivation is preferably under conventional conditions, as, for example, about 37° C. for any suitable period of time. For typical tests, a desirable time period is approximately from about 4 to about 24 hours, preferably about 18 hours. For some tests, a desirable time period may range from about 48 to about 72 hours.

The measurement of activation is conveniently accomplished by a determination of surface receptors, for example, surface immunoglobulin, or by measurement of incorporated radioactivity where a radiolabelled precursor has been introduced into the B-cell suspension or culture.

The general directness and simplicity of the technique of this invention makes possible the formulation of a simple diagnostic kit, packaged to provide the B-cell source, a suitable culture medium, and reagents for assay of the developed polyclonal B-cell activity. In such a kit, the B-cell source and culture medium are preferably combined and provided, for suitable storage awaiting use, as a frozen suspension, conveniently maintained at liquid nitrogen temperature. Thawing of the suspension of B-cells in culture medium is readily accomplished prior to use in the assay.

The following data, descriptive of biological techniques and test results, are exemplary, without limitation, of the method of this invention.

EXAMPLE I

Stimulation of rabbit B-cells determined by maintenance of surface immunoglobulin In the preparation of rabbit lymphoid cells, the tissue was teased and passed through a stainless steel screen. The cells were then filtered through cotton, to remove debris, and a suspension containing $10^6$ viable cells per ml. in RPMI-1640 medium was prepared. The culture medium was supplemented with 5% heat-inactivated rabbit serum. The suspensions were distributed in polystyrene tissue culture flasks, each bottle containing 5 ml. of cell suspension.

In testing for polyclonal B-cell activation by the maintenance of surface immunoglobulin, the cultures were incubated at 37° C. overnight, either without any stimulation, or with lipopolysaccharide (LPS) from *Thyphi murium*, or with the serum sample to be tested. The cells were washed four times in MEM containing 1% bovine serum albumin and 0.02% sodium azide. To determine the percentage of immunoglobulin bearing cells the cell suspension was treated with anti-immunoglobulin allotype-coated sheep erythrocytes. This rosette formation assay is known to parallel the total amount of surface immunoglobulin as detected by radioactive iodinated antibodies. When the B-cells were even minimally activated they maintained a high level of surface immunoglobulin and some 40-50% could be counted as immunoglobulin bearing cells. When they were not stimulated, the percentage of immunoglobulin bearing cells dropped to 10% to 20%. Thus, only two kinds of results were obtained, positive or negative, since the maintenance of surface immunoglobulin was an "all or nothing" phenomenon. When testing for polyclonal B-cell activation the last dilution at which the surface immunoglobulin was maintained was taken as the titer. By this method any polyclonal B-cell activator or T-independent antigen may be detected but not polyclonal T-cell activators or T-dependent antigens. This method of testing for B-cell activation is approximately 1000 times more sensitive than incorporation of radiolabelled precursors in some instances.

The testing of normal donors and patients with rheumatic diseases for the presence of polyclonal B-cell activator in their serum was carried out under double blind conditions. Serum samples were obtained from normal donors and also from patients with rheumatic diseases which were diagnosed according to the criteria of the American Rheumatism Association. For screening, to each 5 ml. of rabbit lymphoid cell culture was added 0.1 ml. of human serum. As a control, some cultures received lippopolysaccharide (LPS) from *Thyphi murium*, a classical polyclonal B-cell activator. The cultures that did not receive any stimulus had a very low level of surface immunoglobulin (about 20%); the cells that received LPS had about 50% immunoglobulin-bearing cells. In cultures receiving normal human serum, the same low level of surface immunoglobulin as in the control was observed (from 10 to 22% immunoglobulin-bearing cells). The addition of serum from patients with rheumatic diseases resulted in the maintenance of surface immunoglobulin to the same extent as in the cultures stimulated with LPS (about 50%). It was found that 19 out of 21 patients with sero-positive rheumatoid arthritis and polyclonal B-cell activator in their serum at the screening dilution tested (1:50). The two patients not showing any activity had clinically inactive rheumatoid arthritis. It was also found that 3 out of 4 patients with lupus erythematosus, and 2 out of the 2 patients with dermatomyssitis had polyclonal B-cell activator in their serum. Again, the patient with lupus erythematosus who did not show activator in his serum had the disease in remission.

In order to determine whether the polyclonal B-cell activator in the serum of patients could be titrated, various dilutions of sera were added to rabbit lymphoid B-cell cultures. Six patients were tested and the titers varied from 1:200 to 1:3200. The data suggested that the amount of activator can vary from one patient to another, and therefore, this technique can be used to determine and follow the level of polyclonal B-cell activator in the serum of patients.

EXAMPLE II

Stimulation of human B-cells determined by incorporation of radiolabelled precursors To obtain cell populations enriched in B-cells, human mononuclear cell suspensions were prepared by Ficoll-hypaque buoyant density centrifugation and the cells were washed three times. Neuraminidase-treated sheep red blood cells (SRBC) were added to the lymphocyte population to achieve a ratio of 100 erythrocytes per lymphocyte in a medium composed of 100% fetal calf serum. The cells were centrifuged at 1000 r.p.m. for 5 minutes, incubated at 37° C. for 15 minutes, incubated in ice for 30 minutes, gently resuspended in RPMI-1640 medium and centrifuged for 15 minutes at 2000 r.p.m. on Ficoll-hypaque medium. The cells at the interface were collected and washed three times in Eagle's minimal essential medium (MEM). The percentage of B-cells was determined by rosetting with *Brucella melitensis*. The cell populations obtained by these methods contained 81%-85% cells that bound *B. melitensis* and less than 6% cells that bound SRBC; the original lymphocyte population contained 16%-24 % cells that bound *B. melitensis* and 71%-80% cells that bound neuraminidase-treated SRBC. Thus, the former population was considered B-cell rich population and the latter T-cell rich population.

In testing for polyclonal B-cell activity by incorporation of radiolabelled precursors, human Ficoll-hypaque purified lymphocytes or nude mouse spleen cells, at a concentration of $10^6$ cells per ml. in RPMI-1640 medium, supplemented with serum as described above, were incubated in microtiter plates, each well containing 200 microliters of suspension. Ten microliters of patient serum or its fractions were added and, after 72 hours, $^3$H-thymidine or $^{14}$C-uridine was added. The cells were collected on the fourth day, using an automatic multiple harvester, and the incorporation of $^3$H or $^{14}$C was determined in a Packard liquid scintillation spectrometer.

It was found that when activity could be demonstrated by the maintenance of surface immunoglobulin at high titers, an increased $^{14}$C-uridine incorporation also occurred. However, when the serum was obtained from patients with undetectable or low activator titers (1:200 or less) the mitogenic activity was barely detectable. None of the normal human sera tested showed any mitogenic activity by this assay.

Patient serum was also tested on T-cell-rich and B-cell-rich populations. The response of the B-cell-rich population to patient serum was slightly higher than that of the T-cell-rich population, suggesting that B-cells were stimulated, but not ruling out the possibility that T-cells also contributed to the response. When the cells were examined under a microscope, in the presence of 1% trypan blue, a large number of large blastic lymphocytes were seen only when the cells had been stimulated by patient serum or by one of the mitogens. From this it was concluded that human lymphocytes, and primarily B-lymphocytes, are stimulated in a polyclonal manner by a factor present in patient serum.

EXAMPLE III

Stimulation of human B-cells determined by maintenance of surface immunoglobulin In order to show that the polyclonal B-cell activator in the serum of patients with rheumatic diseases was also active on human lyphocytes there was tested, by the same method, the ability of the serum samples to maintain the surface immunoglobulin on human tonsil B-lymphocytes. This experiment was also done under double-blind conditions. Serum samples from five patients with rheumatoid arthritis that had been tested on rabbit lymphoid B-cell cultures (four had activator and one did not) were also tested on human tonsil lymphocytes. The test was done in the presence of 5% pooled human serum (from 8 different normal individuals) by adding 0.1 ml. of patient serum to each 5 ml. of cell suspension. The cells were incubated overnight at 37° and the presence of surface immunoglobulin was determined by rosetting with human erythrocytes coated by chromic chloride with rabbit anti-$\kappa$ and anti-$\lambda$ light chain antibodies.

Anti-human light chain antibodies were prepared in rabbits by using Bence Jones proteins as previously described (Mayer et al., 1975). The rabbit anti-$\alpha_2$-macroglobulin was purchased as a lyophilized preparation and its specificity tested by immunoelectrophoresis against whole human serum.

By this procedure, the tonsil cells showed 37% immunoglobulin-bearing cells before they were cultured and 35% after the cells were cultured in the presence of LPS. The cells also maintained the same ratio of $\kappa$-bearing to $\lambda$-bearing B-cells, their sum being equal to the total immunoglobulin-bearing cells, ruling out passive attachment of immunoglobulin from the serum. When no nitrogen was added only 8% of the cell formed rosettes. The same four sera that had detectable activator when tested on rabbit lymphocytes also had activator when tested on human tonsil cells. Similarly, the serum which was negative on rabbit lymphoid cells was also negative on human tonsil cells. The positive control was represented by cultures stimulated with 10 pg/ml. of LPS and the negative controls by cultures to which normal human serum had been added. Thus, in the serum of patients with rheumatic diseases, there is a polyclonal B-cell activator which can stimulate human B lymphocytes to maintain their surface immunoglobulin.

EXAMPLE IV

In further demonstration that the mitogen in the patient serum is indeed a B cell mitogen, serum samples from patients and from normal donors were added to nude mouse spleen cells and the uptake of $^3$H-thymidine was determined after culturing for four days. Cells receiving patient serum were substantially stimulated by patient serum but not by normal serum. When the nude mouse spleen cells were examined under the microscope, in the presence of 1% trypan blue, the cultures receiving patient serum or LPS were found to be composed of a cell population which was over 90% viable and contained substantially only large blastic lymphocytes. The cell populations cultured in the presence of normal human serum had a very low viability (less than 5% viable cells) and no blast cells could be detected among 200 cells counted. This low viability in the absence of stimulus was in agreement with previous results with rabbit lymphocytes cultured for several days in the absence of mitogen.

EXAMPLE V

The molecular nature of the polyclonal B-cell activator in patient serum

In order to determine the molecular nature of the activator responsible for activity in the serum of patients with rheumatic diseases, there was prepared a pool of five serum samples containing polyclonal B-cell activator. This pooled serum was fractionated on a Sephadex G-200 column and 3 major peaks were obtained. The contents of each peak was tested by immunelectrophoresis. The first peak contained primarily $\alpha_2$-macroglobulin and immunoglobulin M, the second peak contained mainly immunoglobulin G, and the third peak mainly albumin. The protein concentration in each peak was adjusted to approximately 0.5 mg/ml. (0.8 OD at 280 nm). Various amounts of these fractions were added to rabbit spleen cell cultures in order to determine their activity by the maintenance of surface immunoglobulin. Activity could be detected only in the first peak, by maintenance of surface immunoglobulin (titer of 1:100) and by inducing blast transformation in human B-cell-rich population (stimulation index of 10 for $^{14}$-C-uridine incorporation), in T-cell-rich population (stimulation index of 4) or in nude mouse spleen cell cultures (stimulation index of 30 for $^3$H-thymidine incorporation). The second and third peaks did not contain enough activity to be detected even at the dilution of 1:10 and did not induce any detectable blast transformation. These results clearly showed that the polyclonal B-cell activator was associated with the fraction containing the macroglobulins.

In order to determine whether the activity was associated with $\alpha_2$-macroglobulin or with immunoglobulin M, samples of the macroglobulin peak were treated with either rabbit anti-light chain antibodies or with rabbit anti-$\alpha_2$-macroglobulin. A precipitating amount of antiserum was added to each sample. The precipitates were removed by centrifugation and subsequent filtration through millipore filters and the two samples were tested for polyclonal B-cell activator activity by both the maintenance of surface immunoglobulin and by blast transformation in human and nude mouse lymphocyte cultures. When the immunoglobulins were precipitated, activity remained at the same titer by the maintenance of surface immunoglobulin and its blastogenic activity was even increased. However, when $\alpha_2$-macroglobulin was precipitated, activity became undetectable.

To further rule out the possibility that antibodies or immune complexes were responsible for the polyclonal B-cell activation observed, immune complexes of rabbit anti-human light chains and human serum in slight antigen excess were prepared and tested their polyclonal B-cell activity in rabbit lymphoid cell cultures by the maintenance of surface immunoglobulin assay. No activity could be detected. The PBA containing pool of patient sera was also absorbed on anti-light chain antibody Sepharose immunosorbent columns. After repeated absorptions, the titer of the activator remained unchanged (1:800), although the total amount of surface immunoglobulin was reduced about 4 times.

Accordingly, it is very unlikely that immune complexes or immunoglobulins serve as active agents in the assay for polyclonal B-cell activation. Therefore, it is concluded that in patients with rheumatic diseases an $\alpha_2$-macroglobulin, or $\alpha_2$-macroglobulin-associated agent, is responsible for the polyclonal B-cell activation.

We claim:

1. A method for diagnosing rheumatoid arthritis and related diseases in a human patient, comprising the steps of:
   (a) providing a lymphocyte population, comprising B-cells, suspended in a culture medium;
   (b) adding to the B-cell suspension with mixing a portion of serum taken from said patient;
   (c) cultivating in vitro the resulting mixture of serum and B-cell suspension; and
   (d) determining the extent of polyclonal lymphocyte activation exhibited by the B-cells in said mixture.

2. The method of claim 1 wherein the lymphocyte population is selected from the class consisting of rabbit B-cells, human B-cells, and mouse spleen B-cells.

3. The method of claim 1 wherein the cell suspensions are cultivated at about 37° C. for a period of from about 4 hours to about 72 hours.

4. The method of claim 1 wherein the polyclonal lymphocyte activation is determined by a measurement of the presence of surface receptors.

5. The method of claim 4 wherein the polyclonal lymphocyte activation is determined by a measurement of the presence of surface immunoglobulin.

6. The method of claim 1 wherein the extent of polyclonal lymphocyte activation is measured by incorporating a radio-labelled precursor into the B-cell culture.

7. The method of claim 1 wherein the serum taken from the subject patient is fractionated and a selected fraction thereof is added to the B-cell suspension.

8. The method of claim 1 wherein a lymphocyte population, comprising mouse B-cells, is suspended in a medium comprising normal human serum and radio-labelled precursors, mixing with the suspension a sample of patient serum, cultivating the mixture, and determining the extent of polyclonal lymphocyte activation.

9. A diagnostic kit, for assay of polyclonal lymphocyte activation of B-cells, as a determinant for rheumatoid arthritis in a subject patient, comprising:
   (a) a packaged suspension of B-cells in a culture medium;
   (b) means for adding to said suspension a sample of patient serum, or fraction thereof; and
   (c) means for determining, after incubation, the proportion of cells having surface immunoglobulin.

10. The diagnostic kit of claim 9 wherein the packaged suspension of B-cells in a culture medium is provided as a frozen suspension maintained at substantially liquid nitrogen temperature.